United States Patent
Kashi et al.

(10) Patent No.: US 10,064,701 B1
(45) Date of Patent: Sep. 4, 2018

(54) DUAL-ENDED DISPOSABLE TRIPLE TOOL DENTAL APPLICATOR APPARATUS

(71) Applicants: Ajay Kashi, Rochester, NY (US); Iswara Prasad Parvathaneni, Pittsford, NY (US)

(72) Inventors: Ajay Kashi, Rochester, NY (US); Iswara Prasad Parvathaneni, Pittsford, NY (US)

(*) Notice: Subject to any disclaimer, the term of this patent is extended or adjusted under 35 U.S.C. 154(b) by 0 days.

(21) Appl. No.: 15/480,675

(22) Filed: Apr. 6, 2017

(51) Int. Cl.
| | |
|---|---|
| A61C 3/00 | (2006.01) |
| A61C 5/00 | (2017.01) |
| A61C 3/08 | (2006.01) |
| A61C 5/60 | (2017.01) |
| A61C 5/62 | (2017.01) |

(52) U.S. Cl.
CPC ............ A61C 3/00 (2013.01); A61C 3/005 (2013.01); A61C 3/08 (2013.01); A61C 5/00 (2013.01); A61C 5/60 (2017.02); A61C 5/62 (2017.02)

(58) Field of Classification Search
CPC .... A61C 3/00; A61C 5/60; A61C 5/62; A61C 3/005; A61C 3/08; A61C 5/00
See application file for complete search history.

(56) References Cited

U.S. PATENT DOCUMENTS

| | | | | |
|---|---|---|---|---|
| 4,767,332 A | * | 8/1988 | Weissman | A61C 5/35 433/225 |
| 5,150,495 A | * | 9/1992 | Discko, Jr. | A46B 5/0075 15/106 |
| 6,049,934 A | * | 4/2000 | Discko | A46B 5/00 15/105 |
| 6,634,051 B1 | * | 10/2003 | Dragan | A46B 5/00 15/105 |
| 6,957,958 B2 | * | 10/2005 | Rowe | A61C 5/60 206/209 |
| 9,463,287 B1 | * | 10/2016 | Lorberbaum | A61M 5/422 |
| 2002/0027088 A1 | * | 3/2002 | Discko, Jr. | A61M 35/003 206/229 |
| 2003/0093026 A1 | * | 5/2003 | Petrich | A61C 5/62 604/1 |
| 2004/0267181 A1 | * | 12/2004 | Tuite | A61B 10/02 604/1 |
| 2005/0069373 A1 | * | 3/2005 | Parikh | A46B 9/005 401/183 |
| 2005/0100860 A1 | * | 5/2005 | Kameli | A61C 3/00 433/144 |
| 2006/0271061 A1 | * | 11/2006 | Beyar | A61B 1/00071 606/105 |
| 2011/0024462 A1 | * | 2/2011 | Teys | A47G 21/004 222/192 |

* cited by examiner

Primary Examiner — Nicholas Lucchesi
(74) Attorney, Agent, or Firm — Sonya C. Harris; Invention Services

(57) ABSTRACT

A dual-ended triple tooled dental applicator apparatus, comprising a plurality of tools with at least one being removably attached. The dental apparatus further comprises a unitary contiguous device having three distinct tools with one tool being detachably connected by a scribe line forming a frangible removable portion thereof. The multi-functioned dental apparatus is comprised of a lightweight but rigid materials (e.g., plastic), which allows the dentist to efficiently use the same tool for working with and applying different materials to a patient's teeth. Upon completion of a given procedure, the end with the frangible portion, as well as the entire device after use, are rendered readily disposable.

9 Claims, 4 Drawing Sheets

DUAL-ENDED DISPOSABLE TRIPLE TOOL DENTAL APPLICATOR APPARATUS

FIELD OF INVENTION

The present invention relates to a disposable applicator for applying different materials, and in particular to a disposable dental applicator having multiple tools used to apply dental materials.

BACKGROUND

Applicators such as brushes, foam pads, cotton fiber or other applicators, are used to apply a variety of materials in many applications. Such applicators are of particular use in dentistry for applying various dental materials. as many dental procedures require various dental materials, such as sealants, bonding agents and the like, to be painted onto a tooth in thin, even coatings or layers. Also, it invariably happens that after several uses, the dental materials would tend to accumulate onto reusable dental applicators resulting in a time-consuming cleaning problem. Moreover, because of the need for sterilization to prevent cross-contamination between patients, the use of multiple applicators requiring frequent cleaning have been used. Because the dental materials in current use include various materials that cure in a relatively short period, cleaning and/or sterilization of such dental devices proves difficult, costly and in some cases unsafe. With the advent of contagious and dangerous communicable diseases and the quick setting dental materials, a disposable multi-functioning, multi-tooled applicator is desirable.

As a result, it is necessary to produce a double-ended triple-tooled dental applicator that is efficient and easy to handle at a low cost.

SUMMARY OF THE INVENTION

The present invention addresses the above-described deficiencies and others as described further below. Specifically, the present invention provides a dual-sided multi-use triple tooled dental applicator apparatus that is disposable.

In accordance with an aspect of the present disclosure, the instant invention provides a low cost, easy to manufacture, disposable dental tool comprised of lightweight but sufficiently rigid, readily available material such as plastic.

The instant invention advantageously allows for the ability of at least three separate applicator tools all within a unitary body with a removably detachable tool providing enhanced versatility and faster procedures.

In accordance with an aspect of the present disclosure, the instant invention provides a double ended, inexpensive, easily disposable device providing various tools that facilitate multiple functions within a unitary apparatus.

In accordance with another aspect of the present disclosure, the instant invention provides a multiple function applicator apparatus with enhanced gripping means for facilitating increased safety, speed and efficiency with performing dental procedures.

In accordance with another aspect of the present disclosure, the instant apparatus is a lightweight uncomplicated structure comprised of frangible tool that is easily discarded after use and is made of readily available materials allowing for easy and low cost manufacture.

In the description herein, numerous specific details are provided, such as examples of components and/or methods, to provide a thorough understanding of embodiments of the present invention. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

BRIEF DESCRIPTION OF THE DRAWINGS

Embodiments of the present disclosure are described herein with reference to the drawings, in which.

The novel features which are characteristic of the invention, as to organization and method of use, together with further objects and advantages thereof, will be better understood from the following disclosure considered in connection with the accompanying drawings in which one or more preferred embodiments of the invention are illustrated by way of example. It is to be expressly understood, however, that the drawings are for the purpose of illustration and description only and are not intended as a definition of the limits of the invention.

As used herein, the term "comprises" refers to a part or parts of a whole, but does not exclude other parts. That is, the term "comprises" is open language that requires the presence of the recited element or structure or its equivalent, but does not exclude the presence of other elements or structures. The term "comprises" has the same meaning and is interchangeable with the terms "includes" and "has". The term set has the meaning of one or more of said element. Furthermore, any use of the term "or" as used herein is generally intended to mean "and/or" unless otherwise indicated. Combinations of components or steps will also be considered as being noted, where terminology is foreseen as rendering the ability to separate or combine is unclear.

BRIEF DESCRIPTION

Figure 1:
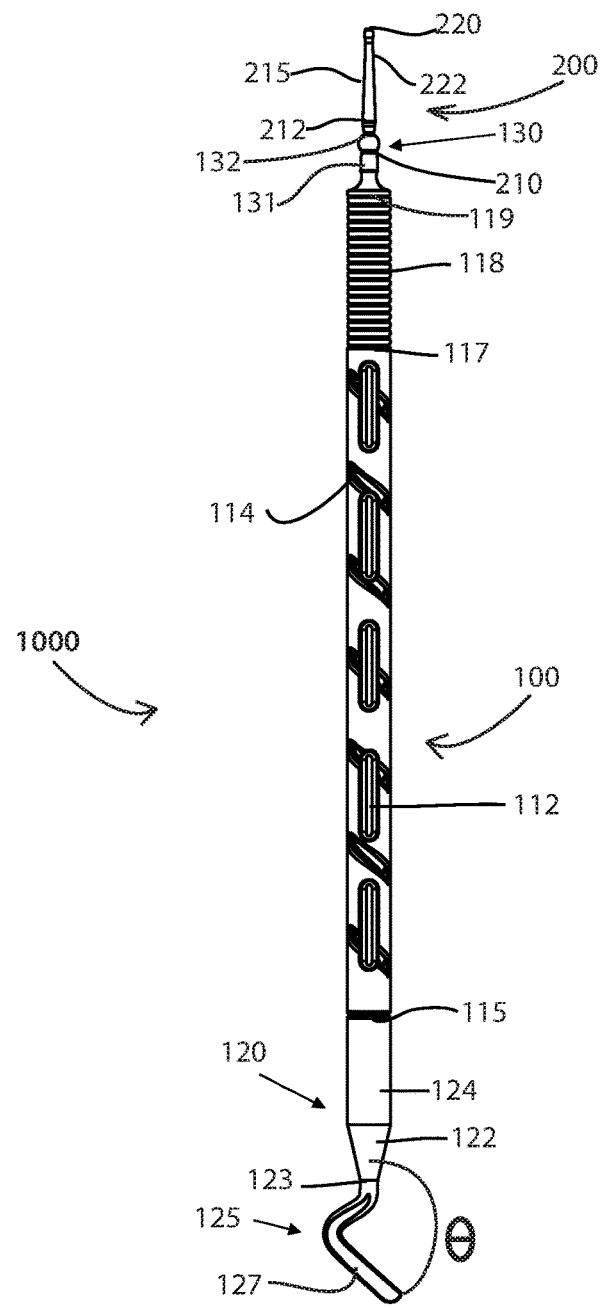
FIG. 1 is an elevational side diagrammatic view of the disposable triple tool dental applicator, illustrating all three tools attached in accordance with an embodiment of the present invention.
Figure 2:
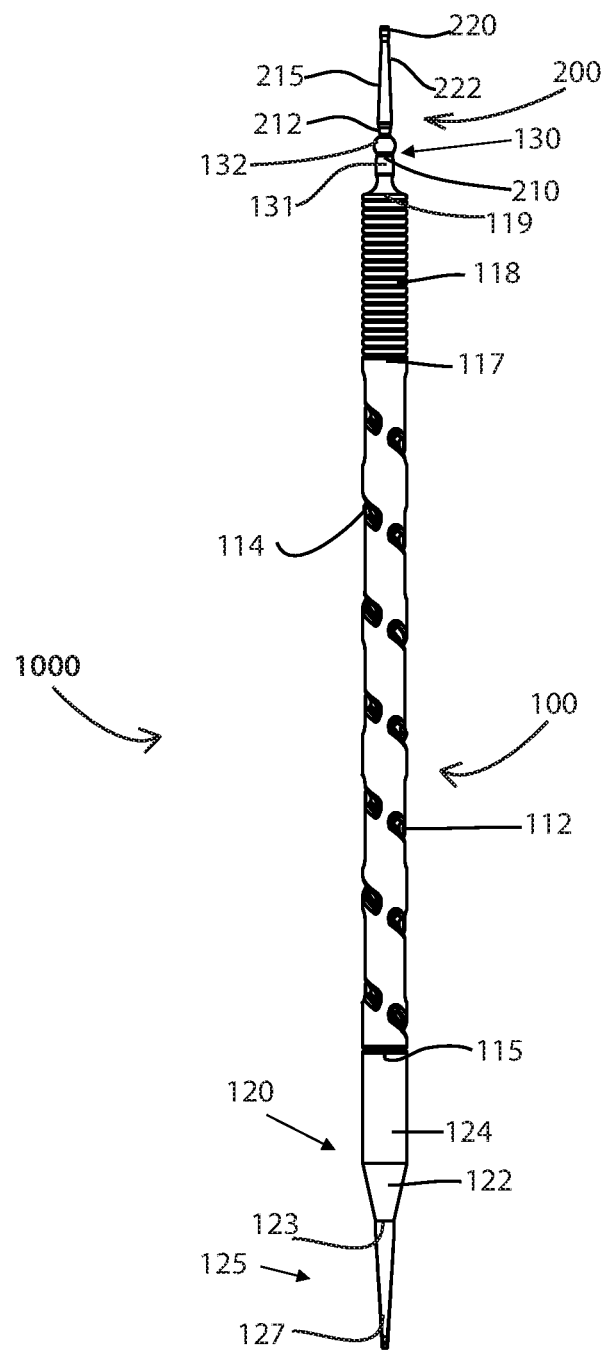
FIG. 2 is an elevational rear diagrammatic view of the disposable triple tool dental applicator, illustrating all three tools attached in accordance with an embodiment of the present invention.
Figure 3:
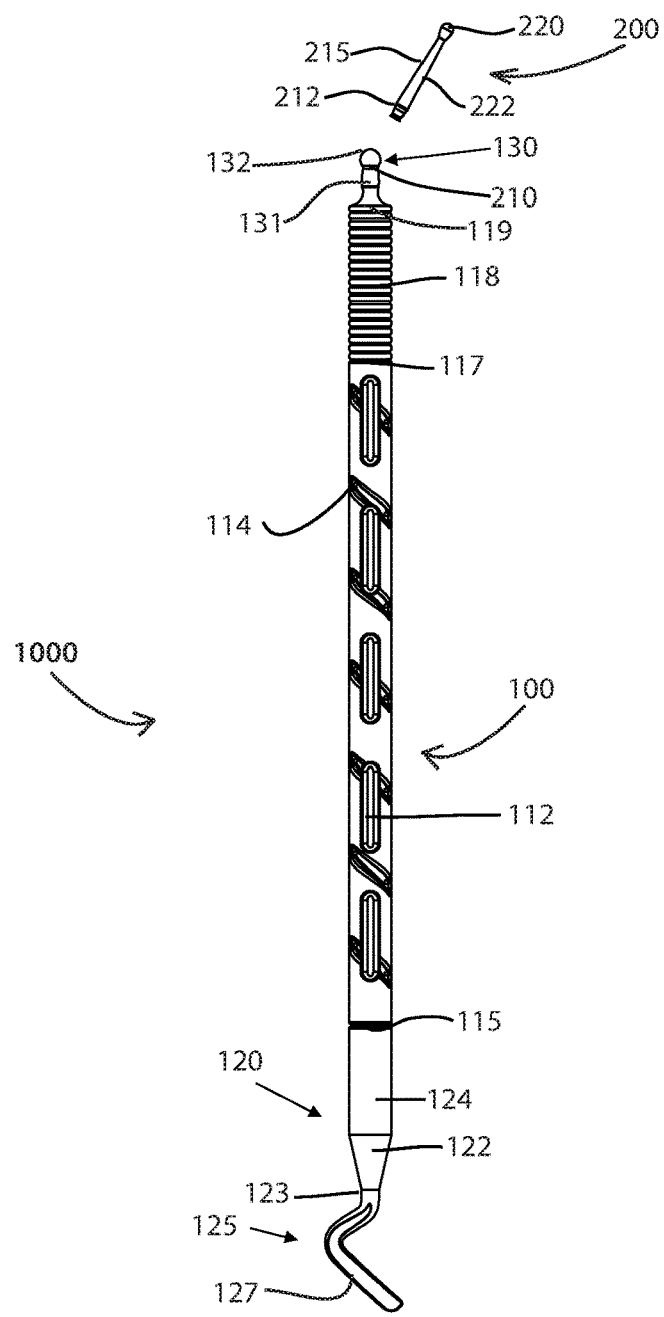
FIG. 3 is an elevational side diagrammatic view of the disposable triple tool dental applicator, after being separated in accordance with an embodiment of the present invention.
Figure 4:
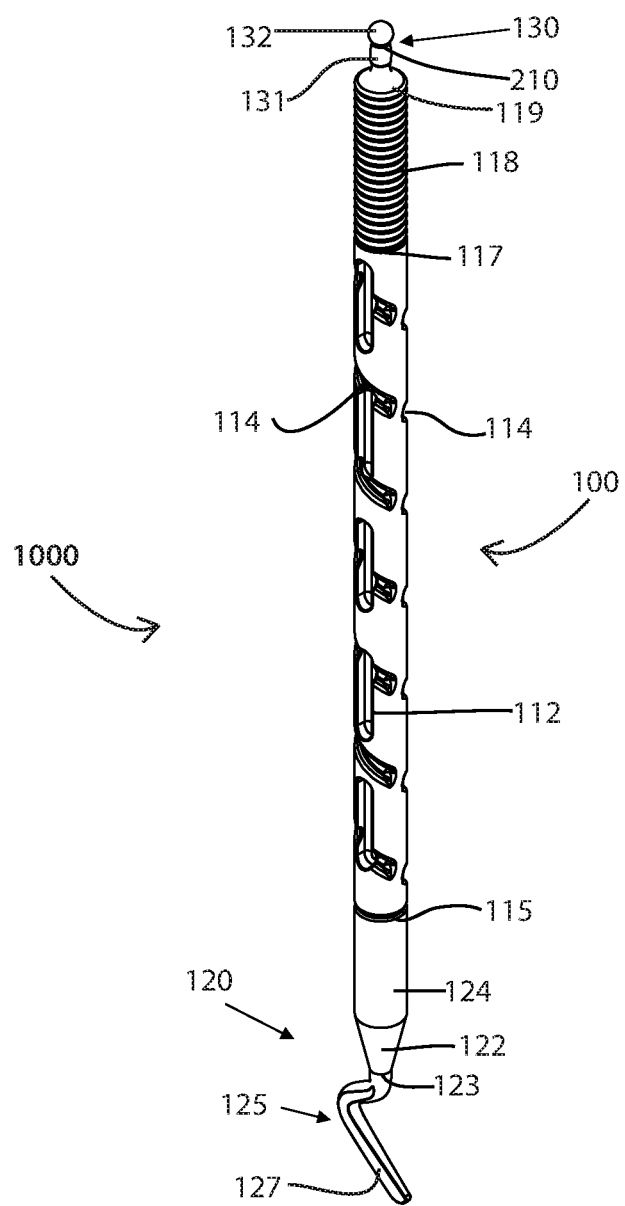
FIG. 4 is a perspective view of the disposable triple tool dental applicator, illustrating the dual tool applicator with the third tool removed in accordance with an embodiment of the present invention.

FIGS. 1-4 illustrate a disposable triple-tooled dental applicator apparatus. FIG. 1 an elevational side diagrammatic view of the tri-tool applicator (TTA) 1000, which is a contiguous, unitary multi-use dental tool apparatus comprised of three distinct tools. FIG. 2 shows an elevational rear diagrammatic view of the TTA 1000, illustrating all three tools attached. FIG. 3 is an elevational side diagrammatic view of the TTA 1000, after being separated, and FIG. 4 is a perspective view of the dual tool applicator (DTA) 100, which remains after the detachment and removal of the frangible tool.

The dual tool applicator (DTA) 100 comprises a cylindrical handle 110 having dental application tools on opposite ends wherein the first end comprises two tools removably attached to one another, and the opposite end comprises a third tool which is offset angularly from them all. Extending from the cylindrical handle 110 of the first end of the DTA 100 is a set of two tools being the ball burnisher 130 (or condenser) and the frangible brush tool 200. A filling instrument tool 120 extends from the handle 110 on the opposite end of the DTA 100 and is offset angularly from the handle 110 and other tools. The ball burnisher 130 and frangible brush tool 200 are each coaxial with respect to one another as well as the handle 110. The frangible brush tool 200 and the ball burnisher 130 are detachably connected by a scribe line 210 that circumscribes the entire periphery of said frangible brush tool 200 forming a scored line for detaching along the scribe line 210 by applying a normal (perpendicular) force against the proximal end 222 thereof. The scribe line 210 is a cut or indentation extending radially into and between the disposable frangible brush tool 200 around its circumference and the uppermost tip surface of the ball burnisher 130, so as to form a readily separable or frangible portion or means for separating the two respective tools (130, 200). The scribe line 210 is located at the base or most distal portion 212 of the frangible brush tool 200. Extending from the most distal portion 212, a handle 215 is formed having a continuously reducing diameter for manipulation of the frangible brush tool 200 during use. The frangible brush tool 200 has a length of approximately one inch in a preferred embodiment, and has a microbrush tip 220 at the most proximal end 222 of the handle 215. The reducing diameter of the handle 215 is at its largest at its most distal portion 212 and smallest at its most proximal end 222. On the proximal end 222 of the most reduced diameter portion of the handle 215 is a microbrush element 220. As best seen in FIG. 3, after the frangible brush tool 200 is used, it is easily detached by the application of normal forces by the user, and discarded leaving the remaining dual tool applicator (DTA) 100, as shown in the perspective view of FIG. 4. Upon completion of a given procedure, the frangible brush tool 200 is rendered readily disposable. Prior to detachment, the TTA 1000 has a length of approximately 6-7 inches in a preferred embodiment, extending from its most proximal end at 119 to its most distal end at 115.

The handle 110 of the DTA 100 is substantially cylindrical and extends along a longitudinal axis and has a central axis along its length, and a width of approximately a quarter inch thick. To facilitate gripping and handling during dental procedures, the DTA 100 has three sets of frictional enhancement means. This is a great convenience to the user or dentist working in a wet environment with saliva, blood, detritus, and other debris culminating from the procedure. A first set of frictional enhancement means abuts the ball burnisher tool 130 at the more proximal end 119 of the handle 110, and comprises an array of a plurality of circumferential grooves 118 or ridges. The second set of frictional enhancement means extend longitudinally and comprise a set of elongated grooves 112 along the entire length of the body of the handle 110 on opposite sides thereof (best seen in FIG. 2). The elongated grooves 112 are a set of repeating cored indentations each having approximate dimensions of about 0.07 inches in depth, 0.9 inches wide and 0.4 inches long in a preferred embodiment. The third set of frictional enhancement means are spiral about the entire length of the handle 110 and comprise a set of spiral grooves 118, having an approximate dimension of 0.03 inches deep, spiraling at an angle of 0.23 degrees relative to the central axis of the handle 110, and extend about the entire length thereof from the proximal end 117 to the distal end 115. Wherein the plurality of circumferential grooves 118 are perpendicular to the elongated grooves 112, the set of spiral grooves 118 extend diagonally relative to the elongated groves 112, and in some instances may intersect thereof. The intricacies of the frictional enhancement means further facilitates ease in turning and rotating the TTA 1000 about the work environment as well as inverting the tool about opposite ends depending on which of the three tools the dentist or user needs during the procedure.

The ball burnisher 130 applicator tool has a tapered portion 131 with a reducing diameter, which further facilitates gripping and manipulation while using the condenser during a procedure. This tapered portion 131 also facilitates fine motor movement of the fingers by the dentist or user for condensing bonding materials and the like during procedures and helps to improve visibility when working in small spaces, such as between or within teeth. The ball burnisher 130 is formed as a spherical ball in the preferred embodiment, however it may take the other geometric shapes.

The filling instrument tool 120 located on the opposite end of the handle 110 extends from the distal most portion 115. The filling instrument tool 120 has essentially three parts with a proximal elongated, cylindrical longitudinal handle portion 124 extending from the handle 110 from its most distal portion 115. The second part comprising a tapered conical portion 122 having a reducing diameter (with the smallest diameter at the most distal end 123), for facilitating handling and fine motor manipulation with the fingers of the dentist or user. Both the cylindrical longitudinal handle portion 124 and the conical tapered portion 122 share the same central axis of the handle 110, ball burnisher 130, and frangible brush tool 200. The tapered conical portion 122 helps to improve visibility when working in relatively small areas.

A spatula tool 125 extends from the most distal end 123 of filling instrument tool 120 at an offset angle ø of approximately 130 degrees, (plus or minus 5 degrees) relative to the central axis of the handle 110, ball burnisher 130, and frangible brush tool 200. The spatula 125 has flat surfaces 127 on both sides (as best seen in FIGS. 2 and 4). The spatula 125 has a grooved recess 126 formed on both sides of the spatula 125 at the upper end thereof closest to the most distal end 123 to facilitate gripping and manipulation of the tool while being used by the dentist or user. The spatula 125 has dimensions of a length of approximately an inch with a width of approximately a tenth of an inch and approximately 0.03 inches in width in a preferred embodiment.

The TTA 1000 having double and triple tools on either end of the apparatus always provides at least two tools for use at any one time during procedures whether the frangible brush tool 200 is attached or not. Thus the double-ended applicator permits the dentist to quickly rotate the apparatus along the procedure, greatly reducing the time needed to apply the various materials, which enhances efficacy. Accordingly, the dentist can alternately apply two or more different materials to a single patient quickly and easily with minimum waste of time and materials, greatly reducing cost to the patient.

The TTA 1000 may be molded of a hard durable and rigid, solid plastic material. For example, the entire TTA 1000 may be comprised of a suitable medical grade plastic having sufficient strength and rigidity, such as a Shore D rigid and hard plastic of a sufficient durometer to withstand the normal, tensile, tangential and other forces used when handling the apparatus during procedure. Although the TTA 1000 is a disposable device, it may also be comprised of plastic materials that can be sterilized in an autoclave in the event that multiple uses are warranted.

Each of the distinct parts of the TTRA 1000 including the filling instrument tool 120, the bonding brush 220, and frangible brush tool 200 as well as the handle 110 may have colors that is distinct from one another. For example, handle 110 may be white, and the filling instrument tool 120 may be black, the bonding brush 220 and the frangible brush tool 200 could be green. However, any combination of distinct colors may be used. This is so that a user, such as a dentist, can easily distinguish either end. This is advantageous when different materials are being used for each applicator end.

Accordingly, it should be appreciated that the present invention, in providing a relatively inexpensive, disposable applicator handle having an integrally formed and removable applicators on either end greatly reduces cost and waste. Additionally, the present invention, by providing a scribe or score line intermediate either end provides the user with flexibility in using either a double ended applicator or two or three independent and separate applicator tools. While a scribe line or score line has been illustrated, it should be appreciated that any structure that permits the applicator handle to be separated into a first and second portion would be equivalent.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. For example, it should be appreciated that other geometric shapes of the handle portions, such as for example, hexagonal, may be used to form the shapes of the handle 110, both the cylindrical longitudinal handle portion 124 and the conical tapered portion 122 of the filling instrument tool 120, as well as the handle portion including the set of spiral grooves 118. Moreover, the condenser or ball burnisher 130 may be formed of other shapes, such as for example an ovoid shape.

As indicated, these modifications may be made to the present invention in light of the foregoing description of illustrated embodiments of the present invention and are to be included within the spirit and scope of the present invention.

What is claimed is:

1. A disposable triple tool dental applicator apparatus comprising:
    a cylindrical handle having a first and a second end, comprising a set of applicator tools on either end;
    a first applicator tool extending coaxially from said first end of said cylindrical handle;
    a second frangibly detachable applicator tool extending coaxially from said first applicator tool on said first end of said cylindrical handle; and
    a third applicator tool extending from the second end of said cylindrical handle and offset at a fixed angle relative to the central axis of both said cylindrical handle and said first and second detachable tool applicators; and wherein
    said three sets of frictional enhancement means comprise a first plurality of circumferential grooves located at the first end of said cylindrical handle,
    a second plurality of spiraling grooves descending along and circumferentially about the length of said cylindrical handle for enhancing grip and reducing slippage while being held during use, and
    a third plurality of longitudinal grooves on opposite sides of said cylindrical handle.

2. The disposable triple tool dental applicator of claim 1 further comprising:
    a scribe line circumscribing the entire periphery of and extending radially into said second applicator tool forming a frangible portion between said second detachable
    applicator tool and said first applicator tool and being detachably connected thereto.

3. The disposable triple tool dental applicator of claim 2 wherein:
    the first applicator tool comprises a ball burnisher condenser tool having a spherically formed tip.

4. The disposable triple tool dental applicator of claim 3 wherein:
    the second detachable applicator tool has a proximal and distal end having a continually reducing diameter forming a handle with the proximal end having a smaller diameter than the distal end;
    and said scribe line located at said distal end; and
    a micro dental activator brush on said proximal end.

5. The disposable triple tool dental applicator of claim 4 wherein:
    the third applicator tool comprises a proximal end and a distal end said proximal end having a cylindrical longitudinal portion that tapers into a beveled cylindrical portion at the distal end,
    and wherein said beveled distal end further comprises a spatula tool that is offset from said beveled distal end at a fixed obtuse angle relative to said central axis of said first applicator tool, said second detachable applicator tool and said cylindrical handle.

6. The disposable triple tool dental applicator of claim 5 wherein:
    said cylindrical handle, said first applicator tool, said second applicator tool and
    said third applicator tool are all comprised of hard, rigid plastic materials.

7. The disposable triple tool dental applicator of claim 6 wherein:
    said third applicator tool is offset at an angle of approximately 130 degrees relative to said central axis of said first applicator tool, said second detachable applicator tool and said cylindrical handle.

8. The disposable triple tool dental applicator of claim 7 wherein:
    said plurality of circumferential grooves are perpendicular to said plurality of longitudinal grooves, and said plurality of said longitudinal grooves are diagonal to said plurality of spiraling grooves.

9. The disposable triple tool dental applicator of claim 8 wherein:
    each of the first applicator tool, the second detachable applicator tool and said third applicator tool each comprise a color distinct from one another.

\* \* \* \* \*